(12) United States Patent
Saladin et al.

(10) Patent No.: US 7,092,490 B2
(45) Date of Patent: Aug. 15, 2006

(54) FILTER SYSTEM FOR RADIOLOGICAL IMAGING

(75) Inventors: Jean Pierre Saladin, Bagneux (FR); Serge Muller, Guyancourt (FR); Celine Pawlak, Plaisir (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 69 days.

(21) Appl. No.: 10/757,932

(22) Filed: Jan. 15, 2004

(65) Prior Publication Data

US 2004/0184582 A1 Sep. 23, 2004

(30) Foreign Application Priority Data

Jan. 30, 2003 (FR) ................................. 03 50007

(51) Int. Cl.
*G21K 3/00* (2006.01)
*G02B 7/00* (2006.01)

(52) U.S. Cl. ........................ 378/156; 378/157; 378/37; 356/418; 359/889; 359/892

(58) Field of Classification Search ................. 378/37, 378/156–159; 976/DIG. 435; 359/889, 359/892; 356/418
See application file for complete search history.

(56) References Cited

U.S. PATENT DOCUMENTS

| | | | |
|---|---|---|---|
| 2,405,444 A | 8/1946 | Moreau et al. | |
| 2,814,727 A * | 11/1957 | Gund et al. | 976/DIG. 435 |
| 3,748,487 A | 7/1973 | Edholm et al. | |
| 4,176,916 A * | 12/1979 | Carpenter | 356/418 |
| 4,347,440 A | 8/1982 | Haas | |
| 4,984,258 A * | 1/1991 | Vlasbloem et al. | 378/145 |
| 6,148,062 A * | 11/2000 | Romeas | 378/156 |
| 2002/0186817 A1 * | 12/2002 | Schukalski et al. | 378/156 |

FOREIGN PATENT DOCUMENTS

EP 0 641 544 3/1995
NL 8400845 A1 * 3/1984

OTHER PUBLICATIONS

"Discrete Interference Filter Monochromator" IBM Technical Disclosure Bulleting, Nov. 1976, vol. 19, No. 6, p. 2194-2195.*

* cited by examiner

*Primary Examiner*—Edward J. Glick
*Assistant Examiner*—Krystyna Suchecki
(74) *Attorney, Agent, or Firm*—Cantor Colburn LLP

(57) ABSTRACT

A filtering system for use in, for example, a radiological imaging in a mammography apparatus. The system has a roundabout carrying a set of filtration plates. Each filtration plate is held on the roundabout by a joint. In a parked or stationary position, each plate is vertically suspended and does not contribute to any unacceptable increase in the horizontal space requirement of an X-ray tube. Each filtration plate may be presented in turn before a window for the emission of X-rays from the tube. At this position, the plate is rectified about its joint in order to occupy one position, among several possible positions, that also makes it possible, in this way, to modulate the filtration capacity of the plate.

42 Claims, 1 Drawing Sheet

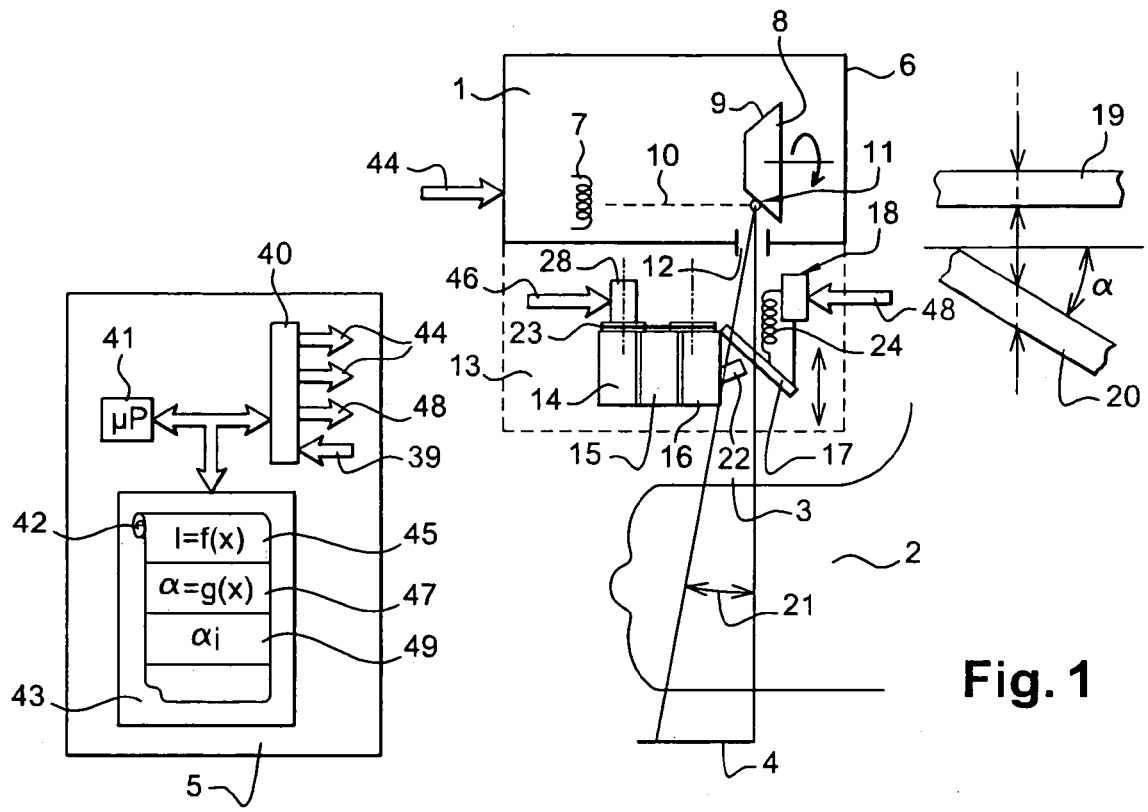
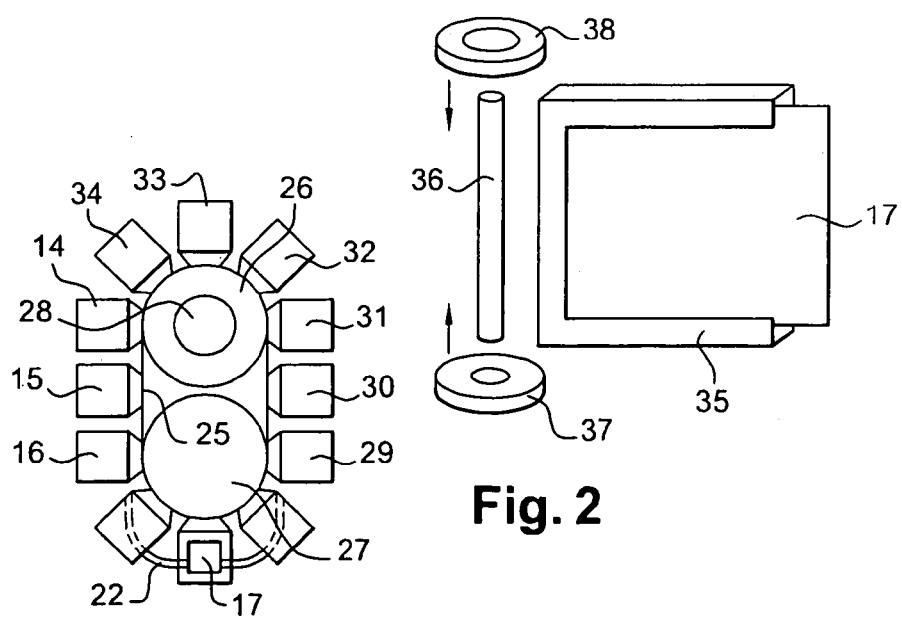

FILTER SYSTEM FOR RADIOLOGICAL IMAGING

This application claims the benefit of a priority under 35 USC 119(a)–(d) to French Patent Application No. 03 50007 filed Jan. 30, 2003, the entire contents of which are hereby incorporated by reference.

BACKGROUND OF THE INVENTION

This invention and embodiments thereof relate to a radiation emitting device and system and in particular an X-ray tube. More particularly, the invention and embodiments thereof related to a tube for a mammography apparatus which tube and apparatus may comprise an improved filtering system.

In radiology, particularly human radiology and particularly in mammography, an X-ray tube is used to irradiate a body and reveal an image of the irradiation on the side of the body that is opposite to the side on which the tube is placed. An X-ray tube comprises a cathode emitting electrons and projecting them at high speed onto an anode as a result of the very high voltage between the cathode and the anode. The anode, subjected to electron bombardment, emits X-rays, in general almost omni-directionally. An X-ray tube is normally shielded except at the position of an emission window through which the useful X-rays are emitted. Due to emission characteristics, variations in the high voltage and the more or less pure nature of the anode material, the frequency spectrum of the X-rays emitted is not a single value but a continuum around a central value.

Developments in radiology have led to attempts to confine this emission spectrum in a narrow band. Depending on hardness and frequency, the X-rays emitted are absorbed in the body by materials of different natures. To characterize a material, especially a tissue in the human body, it is then necessary to use the narrowest possible emission value around an expected value. Since the emitted spectrum is broad, this result is obtained by interposing filters in the path of the X-rays, before they reach the body to be studied. The filters which may be made of aluminum, copper, molybdenum, tungsten, beryllium or rhodium, or even an alloy of these substances, blocks certain parts of the radiation and lets through useful radiation that it is more appropriate to the examination to be made.

There is a known way of positioning a roundabout facing the emission window of the tube. This roundabout is typically a wheel with blades, each blade comprising a filter that, for a given rotational position of the wheel, takes a position before the emission window to bring about the expected filtering. The use of such a wheel is practical because it is not really possible to envisage the manual replacing of the filters at the emission window of the X-ray tube. Since the X-ray tube is subjected to very high voltage, it is necessary to take either preliminary precautions for disconnecting the tube (entailing a loss of time) or additional precautions of electrical installation (increasing the complexity of manufacture of the tube).

However, such a roundabout or filter wheel is not entirely satisfactory. First of all, especially in the context of mammography, this roundabout is a bulky accessory. In the context of a mammography, in practice, the patient places her head beside the x-ray tube side so that her breast can be in the path of the X-rays produced. Experience shows that the patient has to make contortions owing to the fact that the X-ray tube naturally takes up much space. The roundabout takes up even more space and its use is therefore undesirable.

Furthermore, in the field of mammography especially, such a structure is no longer satisfactory for another reason: for a given type of examination, a specific filter may be required. However, the absorption capacity of the filter has to be modified, firstly according to the size of the breast and, secondly, according to the nature of the examination made. In practice, placing a filter of variable thickness in the path of the X-rays does this. Taking five to ten possible thicknesses for each filter soon results in an excessively huge battery of available filters, given that each of these filters, owing to its quality, is particularly costly.

BRIEF DESCRIPTION OF THE INVENTION

An embodiment of the invention provides for changing the filters as a function of the demand.

An embodiment of the invention is a filter system that can be used with means for emitting radiation, such as an X-ray tube. The filter system may be useful for radiological imaging, especially for a mammography apparatus. The means for emitting radiation may comprise a chamber provided with a first and second elements which cooperate for emitting radiation, such as a cathode and an anode, a window in the chamber to let through X-rays emitted by the anode, and an X-ray filtering system. The filtering system may comprise a plurality, i.e., a set of filtration plates held by means for causing a selection of one or more of the filtration plates, such as a distributor, wherein the filtration plates are fixed to the distributor by means of a joint and wherein, facing the window, the filtering system may comprises means for modifying an orientation of a filtration plate around its joint.

BRIEF DESCRIPTION OF THE DRAWINGS

An embodiment of the invention will be understood from the following description and from the appended figures. These figures are given purely by way of example and in no way restrict the scope of the invention. Of these figures:

FIG. 1 shows schematically an X-ray tube;

FIG. 2 shows details of the embodiment of a roundabout that can be used in an X-ray tube;

DETAILED DESCRIPTION OF THE INVENTION

FIG. 1 schematically shows an x-ray tube 1 according to an embodiment of the invention. The tube 1 is shown schematically in a mammography apparatus. An object to be imaged, such as a breast 2, is compressed between a breast-holder tray and a pad (not shown). X-rays 3 radiates breast 2 in order that an image of this radiation may be detected on detector 4. The mammography apparatus, or any other radiology apparatus, comprises a control device 5 capable of controlling its use.

Tube 1 has a chamber 6 provided with a cathode 7 and an anode 8. In one example, the anode 8 is a rotating anode but this is not a necessity. The anode 8 has a track 9 subjected to a bombardment 10 of electrons emitted by the cathode 7. At the position 11 of this bombardment, the target track 9 then emits X-ray radiation. Chamber 6 has an emission window 12 to let through useful X-ray radiation. Chamber 6 is a vacuum chamber and a vacuum-tight plate that however lets through the radiation normally shutters the window 12. The vacuum-tight plate is made, for example, of glass. Chamber 6 of tube 1 is provided with an X-ray filtering system comprising a set of filtration plates 14 to 17 held in a distributor 13.

Distributor 13 is such that the filtration plates 14 to 17 are each held therein by a joint that is, shown in FIG. 2. Facing window 12, the filtering system has means for modifying an orientation of a filtration plate around its respective joint. The means for modifying may be driven, for example, by a motor 18.

In the parked or stationary position, filtration plates 14, 15 and 16 are oriented vertically. In one example, they are suspended and their joint axes are horizontal. These plates then do not extend horizontally and do not cause any unacceptable amount of space to be taken up in the planes parallel to the plane of FIG. 1. As shown at the right-hand side of FIG. 1, motor 18 can be used to give the active filtration plate 17 a variety of orientations, especially a horizontal orientation 19 or a 45° orientation 20. In the horizontal orientation 19, the filtering capacity of the plate 17 is limited by the thickness of the plate 17. This thickness is measured perpendicularly to the plane of the filtration plate 17. On the contrary, in the orientation 20, since the rays cross the plate 17 obliquely, the thickness presented by the plate 17 to X-rays is about $\sqrt{2}$ times greater than the thickness in the orientation 19.

On the one hand, there are very many orientations other than the 0° or 45° orientation possible. As shall be seen further below, numerous orientations may either be continuously adjusted or indexed, so that the plates occupy preferred positions. On the other hand, the dynamic range of variation of this orientation must satisfy questions of space requirement. Owing to the angular aperture 21 of the X-ray beam, the filtering cannot be homogeneous throughout the beam. In this case, either the operation is limited to a range of tilting angles, or the filtration plates are given a shape that is not necessarily flat but curved.

If it is question of space requirement that is the main concern, the gradual raising mechanism 18 may be replaced by a simple ramp 22 (see FIGS. 1 and 2). When the filtration plates 14 to 17 are presented before the window 12 and, solely through the motion of the distributor 13, they will leave their vertical suspended position and, in sliding on the ramp 22, they will take up a position against ramp 22 that depends on its extension. Ramp 22 may be formed by a guide-way placed approximately at mid-height with respect to the plates, horizontally beneath a plane 23 in which the joints of the plates move. At the end of the distributor 13, this guide-way may be transformed into the ramp 22, for example, because its longitudinal extension is longer than the longitudinal extension of a plate-driving wheel.

The raising device may be associated with the ramp 22 so that they complement each other. Many other mechanisms are possible. In particular, the motor-driven mechanism 18 may be replaced by a pusher device mounted in parallel to the ramp 22, between rows of plates such as 14 to 16.

If the tilting or orientation mechanism is designed to be used in systems that do not take solely the vertical position, especially if it is designed for a tomodensitometer in which the orientation of the X-rays rotates about a horizontal axis, a spring 24 may be associated with the raising mechanism or with another mechanism. Spring 24 would be designed to push the plate 17 against the pusher device or ramp 22. Thus, it would not be possible for the plate 17 to be easily disoriented. On the contrary, the plate would be led everywhere to occupy a single position.

Spring 24 as well as the ramp 22 or the raising pusher device is designed so that they do not block the passage of the useful X-rays. Distributor 13 (see FIG. 2) may comprise a roundabout formed by a conveyor 25 continuously circulating on the rim of two wheels, 26 and 27. Motor 28 drives at least one of the two wheels, for example, wheel 26. The rotation axes of the wheels can be substantially parallel to each other and to the main direction of the X-rays emitted by tube 1. At least the distributing wheel 27 has a rotation axis parallel to the main direction of the X-rays. Motor 28 can be a step-by-step motor whose rotational position can be controlled at all times.

FIG. 2 is a diagrammatic view of the plates 14 to 16 in a raised position whereas, in normally they are suspended as also plates 29 to 31, placed on the other side of the roundabout, and returning plates 32 to 34. Plate 17 is shown as being mounted on the ramp 22 and occupying a horizontal position or tilted position, facing the X-rays. A frame 35 with guide-ways mounts each plate, in one example. Frame 35 is attached to a rotation shaft 36. Conveyor 25 carries bearings 37 and 38 that are rotationally mounted on the shaft 36 and enable the frames 35 to move about the axis 36. Conversely, the bearings 37 and 38 can be attached to the frame 35 and the shaft 36 can be attached to the conveyor 25. As a variant, the shaft-and-bearing type joints are replaced by flexible-strip joints, made of plastic for example, fixed firstly to the edge of the frames 35 and secondly to the conveyor 25 by ends of arms of the conveyor.

Filtration plates proper, for example 17, are slid in the guide-ways of frames 35. In the example shown, the roundabout has nine plates made of different types of materials, or if necessary, they are made with gradual increases in thickness that would not be obtained with the variations in tilts 19 and 20 referred to here above. If a thickness of a plate made of a given material must vary between 100% and 400%, it would be appropriate to use two plates, or even three plates to achieve this dynamic range of variation with tilt values ranging from 0° to 60°.

An exemplary installation operates as follows. Using a control keyboard or a trackball, an operator imposes instructed values 39 (see FIG. 1) on an input/output interface 40 of control unit 5. Control unit 5 has a processing unit 41 implementing program 42 contained in a memory 43. Program 42 has means for putting out a command 44 to set the X-ray tube 1. Program 42 is improved by a sub-program 45 for selecting one of the plates of the filtration system. Sub-program 45, which produces a command 46, is applied in practice to the motor 28. Program 42 has another sub-program 47 by which the tilt α of the plate is imposed, by which the thickness presented is modified. Sub-program 47 produces a command 48 applied to raising step-by-step motor 18 so as to modify the tilt of the plate chosen. In one example, sub-program 47 may have a set 49 of tabulated tilt values αi, corresponding to preferred uses of the filtration.

According to an embodiment of the invention the filters are held by joints. In practice, when the filter are in a roundabout magazine, the filters may be suspended and occupy a position. For example they may be oriented vertically. This position does not contribute to an increase in horizontal space requirement. However, at the position of the window, especially in the context of mammography where the X-rays are oriented in a substantially vertical direction and where the emission window is substantially horizontal, the filters are raised around their joint (which is horizontal in this case), and are placed in the path of the radiation.

Different raising mechanisms are possible. However, in one embodiment of the raising mechanism, the raising will not be an "all or nothing" mechanism. The raising may be gradual, or even indexed. Thus, the thickness presented by the filter in the path of the X-rays varies between a minimum thickness of a plate serving as a filter and a substantial proportion, for example 170%, to 200%, of the thickness of the filter plate. When the filter is tilted, it presents the X-rays with an oblique path along its thickness. This oblique path contributes to absorption of the same type but to a different degree, as a function of the raising angle.

One skilled in the art may make or propose various modifications in structure/way and/or function and/or result to the disclosed embodiments and equivalents thereof without departing from the scope of the invention.

What is claimed is:

1. A radiation filtering system suitable for filtering radiation, the system comprising:
   a plurality of filtering plates of which a selected one or more of the plates is configured to be conveyed to and oriented in a stationary position for use;
   means for causing a selection of one or more of the plates, continuous conveyance thereof and stationary positioning thereof;
   the plates being fixed to the means for causing a selection by means of a joint; and
   means for modifying an orientation of a stationary plate about its respective joint.

2. The system of claim 1, wherein the means for causing a selection, continuous conveyance, and stationary positioning, comprises:
   means for rotating one or more of the filtering plate to allow to filtering plate to be oriented at a variety of oblique angles relative to the direction of a filtration path while the filtering plate is parked in a stationary position.

3. An imaging apparatus comprising:
   means for providing a source of X-rays;
   means for detecting the X-rays;
   a filter system for the X-rays comprising:
   a plurality of filtering plates of which a selected one or more of the plates is configured to be placed in a parked stationary position in a path of the X-rays;
   means for causing a selection of one or more of the plates, continuous conveyance thereof and stationary positioning thereof;
   the plates being fixed to the means for causing a selection by means of a joint; and
   means for modifying an orientation of a stationary plate about its respective joint.

4. An X-ray device comprising:
   a chamber provided with first and second elements that cooperate to provide X-rays;
   means for directing the X-rays out of the chamber;
   a plurality of filtering plates of which a selected one or more of the plates is configured to be placed in a parked stationary position in a path of the X-rays;
   means for causing a selection of one or more of the plates, continuous conveyance thereof and stationary positioning thereof;
   the plates being fixed to the means for causing a selection by means of a joint; and
   means for modifying an orientation of a stationary plate about its respective joint.

5. An X-ray tube comprising:
   a chamber provided with a cathode and an anode;
   a window in this chamber to let through X-rays emitted by the anode;
   an X-ray filtering system comprising:
   a set of filtration plates held by a distributor configured for continuous conveyance of the filtration plates and for stationary positioning of the filtration plates, wherein the filtration plates are fixed to the distributor by means of a joint;
   and facing the window, the filtering system comprises a mechanism to modify an orientation of a stationary filtration plate around its respective joint.

6. The tube according to claim 5 wherein the joint comprises a rotation shaft and bearings respectively mounted on an edge of the filtration plate and on an arm of the distributor or vice versa.

7. The tube according to claim 6 wherein the distributor comprises a roundabout formed by a conveyor circulating continuously on the rim of two wheels, the rotational axes of the wheels being parallel to each other and to a direction of the X-rays emitted by the tube.

8. The tube according to claim 6 wherein the distributor comprises a distributor wheel, an axis of rotation of which is parallel to a direction of the X-rays emitted by the tube.

9. The tube according to claim 6 wherein the mechanism comprises a ramp so that the filtration plate rotates about its joint as a result of motion of the distributor.

10. The tube according to claim 6 wherein the mechanism comprises a pusher device to cause the filtration plate to rotate about its joint.

11. The tube according to claim 6 wherein the mechanism comprises a spring to push the filtration plate back towards the pusher device.

12. The tube according to claim 6 wherein the filtration plate is mounted in the filtration system by means of a frame with guide-ways.

13. The tube according to claim 5 wherein the joint comprises a flexible strip for connection between an edge of the filtration plate and an end of an arm of the distributor.

14. The tube according to claim 13 wherein the distributor comprises a roundabout formed by a conveyor circulating continuously on the rim of two wheels, the rotational axes of the wheels being parallel to each other and to a direction of the X-rays emitted by the tube.

15. The tube according to claim 13 wherein the distributor comprises a distributor wheel, an axis of rotation of which is parallel to a direction of the X-rays emitted by the tube.

16. The tube according to claim 13 wherein the mechanism comprises a ramp so that the filtration plate rotates about its joint as a result of motion of the distributor.

17. The tube according to claim 13 wherein the mechanism comprises a pusher device to cause the filtration plate to rotate about its joint.

18. The tube according to claim 13 wherein the mechanism comprises a spring to push the filtration plate back towards the pusher device.

19. The tube according to claim 13 wherein the filtration plate is mounted in the filtration system by means of a frame with guide-ways.

20. The tube according to claim 5 wherein the distributor comprises a roundabout formed by a conveyor circulating continuously on the rim of two wheels, the rotational axes of the wheels being parallel to each other and to a direction of the X-rays emitted by the tube.

21. The tube according to claim 20 wherein the mechanism comprises a ramp so that the filtration plate rotates about its joint as a result of motion of the distributor.

22. The tube according to claim 20 wherein the mechanism comprises a pusher device to cause the filtration plate to rotate about its joint.

23. The tube according to claim 20 wherein the mechanism comprises a spring to push the filtration plate back towards the pusher device.

24. The tube according to claim 20 wherein the filtration plate is mounted in the filtration system by means of a frame with guide-ways.

25. The tube according to claim 5 wherein the distributor comprises a distributor wheel, an axis of rotation of which is parallel to a direction of the X-rays emitted by the tube.

26. The tube according to claim 25 wherein the mechanism comprises a ramp so that the filtration plate rotates about its joint as a result of motion of the distributor.

27. The tube according to claim 25 wherein the mechanism comprises a pusher device to cause the filtration plate to rotate about its joint.

28. The tube according to claim 25 wherein the mechanism comprises a spring to push the filtration plate back towards the pusher device.

29. The tube according to claim 25 wherein the filtration plate is mounted in the filtration system by means of a frame with guide-ways.

30. The tube according to claim 5 wherein the mechanism comprises a pusher device to cause the filtration plate to rotate about its joint.

31. The tube according to claim 30 wherein the mechanism comprises a spring to push the filtration plate back towards the pusher device.

32. The tube according to claim 31 wherein the pusher device is motor-driven and wherein the filtering system receives a command to cause the filtration plate to occupy intermediate positions with respect to the window between two extreme positions.

33. The tube according to claim 31 wherein the filtration plate is mounted in the filtration system by means of a frame with guide-ways.

34. The tube according to claim 30 wherein the pusher device is motor-driven and wherein the filtering system receives a command to cause the filtration plate to occupy intermediate positions with respect to the window between two extreme positions.

35. The tube according to claim 34 wherein the filtration plate is mounted in the filtration system by means of a frame with guide-ways.

36. The tube according to claim 30 wherein the filtration plate is mounted in the filtration system by means of a frame with guide-ways.

37. The tube according to claim 5 wherein the filtration plate is mounted in the filtration system by means of a frame with guide-ways.

38. The tube according to claim 5, wherein the mechanism comprises means for rotating the filtration plate about its joint thereby allowing the filtration plate to be oriented at a variety of oblique angles relative to the direction of the emitted X-rays.

39. An X-ray tube comprising:
a chamber provided with a cathode and an anode;
a window in this chamber to let through X-rays emitted by the anode;
an X-ray filtering system comprising:
a set of filtration plates held by a distributor, wherein the filtration plates are fixed to the distributor by means of a joint;
and facing the window with a filtration plate parked in a stationary position, the filtering system comprises a mechanism to modify an orientation of a stationary filtration plate around its respective joint;
wherein the mechanism further comprises a ramp so that the filtration plate rotates about its joint as a result of motion of the distributor.

40. The tube according to claim 39 wherein the mechanism comprises a pusher device to cause the filtration plate to rotate about its joint.

41. The tube according to claim 39 wherein the mechanism comprises a spring to push the filtration plate back towards the pusher device.

42. The tube according to claim 39 wherein the filtration plate is mounted in the filtration system by means of a frame with guide-ways.

* * * * *